United States Patent
Caboche et al.

(12) 
(10) Patent No.: US 6,280,985 B1
(45) Date of Patent: Aug. 28, 2001

(54) PROCESS FOR THE SEPARATION AND PURIFICATION OF LACTIC ACID FROM A FERMENTATION MEDIUM

(75) Inventors: Jean-Jacques Caboche, Drouvin le Marais; Catherine Fouache, Sailly Labourse; Jean-Christophe Choque, Lille; Pierrick Duflot, La Couture; Eric Dubois, Lestrem, all of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/688,255

(22) Filed: Oct. 13, 2000

(30) Foreign Application Priority Data

Oct. 18, 1999 (FR) .................................................. 99 12972

(51) Int. Cl.$^7$ ....................................................... C12P 7/56
(52) U.S. Cl. ............................................ 435/139; 435/136
(58) Field of Search ...................................... 435/139, 136

(56) References Cited

U.S. PATENT DOCUMENTS

| 4,275,234 | 6/1981 | Baniel et al. . |
| 5,464,760 | * 11/1995 | Tsai et al. . |
| 5,641,406 | 6/1997 | Sarhaddar et al. . |
| 5,681,728 | 10/1997 | Miao . |
| 5,814,498 | 9/1998 | Mani et al. . |

FOREIGN PATENT DOCUMENTS

| 2227398 | 7/1998 | (CA) . |
| 0346983-A2 | * 12/1989 | (EP) . |
| 0 393 818 | 10/1990 | (EP) . |
| 0 483 831 | 5/1992 | (EP) . |
| 63188632 | 8/1988 | (JP) . |
| WO96/41021 | 12/1996 | (WO) . |

OTHER PUBLICATIONS

Narebska et al. Separation of fermentation products by membrane techniques. II. Convertion of lactic acid by electrodialysis (1998) Separation Science and Technology), vol. 33, No. 7, pp. 959–973.*

Boniardi et al. Lactic acid production by electrodialysis, part I: experimental tests (1997) Journal of Applied Electrochemistry, vol. 27, pp. 125–133.*

* cited by examiner

Primary Examiner—Jon P. Weber
Assistant Examiner—Harry J Guttman
(74) Attorney, Agent, or Firm—Henderson & Sturm LLP

(57) ABSTRACT

The present invention relates to a process for the separation and purification of lactic acid from a fermentation medium wherein the lactic acid is totally or partially in the form of a salt or salts. The lactic acid producing microorganisms are separated from the other components of the fermentation medium. This solution is concentrated and then acidified to a pH below or equal to 3. The acidified solution is passed over a cation exchange resin to give a fraction that has maximum of 25% lactic acid salts relative to the dry weight of the solution. This fraction is subjected to bipolar fractionating electrodialysis. The resulting lactic acid is further purified, concentrated and then recovered.

15 Claims, No Drawings

PROCESS FOR THE SEPARATION AND PURIFICATION OF LACTIC ACID FROM A FERMENTATION MEDIUM

TECHNICAL FIELD

The present invention relates to a specific process for the separation and purification of lactic acid from a fermentation medium.

In particular, the present invention relates to a process for the preparation of lactic acid with a quality which enables it to be used not only in sectors such as the fields of food applications and the chemical, agrochemical, plastics and cosmetics industries, but also especially in the fields of pharmaceutical applications.

BACKGROUND

Lactic acid is normally prepared by the fermentation of microorganisms of the genera Lactobacillus (*L. acidophilus, L. delbrüeckii, L. pentosus* etc.), Rhizopus, Bacillus (*B. coagulans* etc.), Streptococcus etc.

However, it is known that the growth, or even the viability, of the majority of these lactic acid-producing microorganisms is inhibited by the drop in the pH of the fermentation medium, this strong acidification of the medium being caused by the production of organic acids, including lactic acid itself.

It is therefore necessary to regulate the pH and it is generally acknowledged that it has to be maintained at a value of between 4 and 7, preferably of more than 4.5, for example of between 5.5 and 6.5, by the addition of bases such as alkali metal or alkaline earth metal hydroxides, or carbonates or bicarbonates.

The lactic acid is therefore present in these fermentation media in the form of salts (sodium, potassium, calcium or ammonium lactates, individually or in a mixture, depending on the base chosen for regulating the pH of the fermentation medium).

Thus all the methods of recovering the lactic acid from the fermentation media have to solve the same difficulties, i.e. separating the lactic acid salt(s), the microorganisms which produced them and the impurities in the fermentation medium (unconsumed sugars and proteins and various kinds of inorganic salts) as well as converting the lactic acid salts to lactic acid in the free form, which also requires the subsequent removal of the corresponding base generated.

Various methods have been proposed for recovering lactic acid from a fermentation medium.

It is quite generally known to purify lactic acid from lactates by the addition of sulfuric acid.

For example, if the pH of the fermentation medium is regulated with carbonates or bicarbonates, the lactic acid in the free form can be recovered by acidification of the medium with sulfuric acid.

The reaction gives rise to the formation of calcium sulfates (gypsum), which precipitate, and to the release of lactic acid in the free form, which can then be extracted with an organic solvent or adsorbed onto a suitable support and then desorbed.

However, the disadvantage of this method, which is otherwise efficient in terms of yield, is the high consumption of sulfuric acid and especially the production of large amounts of gypsum, which presents serious environmental problems in terms of waste treatment and biodegradability.

Patent JP 63/188,632 describes the regulation of the pH of the fermentation medium with zinc hydroxide to give a zinc lactate of low solubility, allowing it to be purified by crystallization.

The major disadvantage here is the need to use hydrogen sulfide, which is not easy to handle; in particular, this process gives poor crystallization yields due to excessive loss of product in the mother liquor.

Another process consists in carrying out an adsorption/desorption with a trialkylamine. For example, patent DE 2,329,480 describes a liquid-liquid extraction (or LLE) process which consists in extracting the lactic acid by means of a water-immiscible organic solvent in the presence of at least one Lewis base such as a tertiary amine. The lactic acid has to be recovered in a second liquid-liquid extraction step, in which it is transferred back into the water.

However, the disadvantage is in the formation of trialkylammonium lactates with pKa values of about 9 to 11, so the energy required to release the acid form is prohibitive.

By extension, any processes which require the decomposition of trialkylammonium salts to the corresponding acids consume large amounts of energy.

The use of $NH_4OH$ or NaOH to regulate the pH of the fermentation medium is also described, said process making it possible to avoid the need for sulfuric acid and to recover the lactates more cleanly in the form of ammonium or sodium lactates. It is then possible to carry out an ultrafiltration step to separate said lactates from the other components of the fermentation medium, and finally to obtain the lactic acid by carrying out a separation step on ion exchange resins.

This process employs membrane and ion exchange methods by which lactic acid cannot be obtained in high purity.

Two approaches were developed to overcome this difficulty: a first approach involves chromatographic separation, especially on a strong cation exchange resin; the second involves separation by concentrating or desalinating electrodialysis and/or by bipolar fractionating electrodialysis.

According to the first approach, it was proposed to bring the medium containing e.g. sodium lactate into direct contact with a strong cation exchange resin of the hydrogen type, in the liquid form, in order to remove the sodium ions.

However, this process consumes large amounts of resins and hydrochloric or sulfuric acids to regenerate said resin, and is difficult to carry out on the industrial scale.

Patent EP 483,831 offers an alternative to this process by carrying out the separation of an organic acid (or organic acids) and inorganic salts using chromatography columns.

The process described consists in cultivating a lactic acid-producing microorganism in a fermentation medium containing glucose as the carbon source, and chromatographing said fermentation medium, containing sugars, inorganic salts and other residual impurities as well as an organic acid (or organic acids), under specific conditions.

More precisely, the process consists in passing said starting fermentation medium, containing the organic acid (or organic acids), through a column containing the cation exchange resin, resulting in the retention of said organic acid (or said acids) on the column. An eluent of the mineral acid type is then passed through in order to desorb any organic acid. In the case where it is desired to separate several organic acids (such as tartaric acid and gluconic acid), an additional step consists in separating the acids from the resulting eluate.

The description states that it is absolutely essential for the pH to be below the pKa of the acid in question.

More particularly, an example is given of a process for the preparation of lactic acid from an *L. delbrüeckii* fermentation medium, the pH of the medium being regulated to 5.8 with NaOH.

The microorganisms are removed from said medium, containing 71 g/l of sodium lactate, and the medium is then acidified to pH 1.6 with sulfuiric acid. Said acidified solution is then passed through a chromatography column in which the cationic resin has first been equilibrated to pH 3.09 by the passage of dilute sulfuric acid. The column is then eluted with more sulfuric acid, still at a pH below the pKa of lactic acid. i.e. below 3.87, making it possible to recover one fraction containing sodium sulfate and another fraction containing lactic acid.

However, this process again requires the use of large amounts of sulfuric acid, both to lower the pH of the fermentation medium and maintain the pH in the chromatography column, and also to adjust the pH of the eluent to a value below the pKa of lactic acid.

The more it is desired to lower the pH, so as not only to limit the proportion of lactic acid salts in equilibrium with the free lactic acid formed, but also to limit the loss of free lactic acid with the impurities (residual sugars, proteins and inorganic salts in the fermentation medium) which are normally eluted in the first fractions of the chromatographic separation, as furthermore deplored in patent EP 483,831, the larger these amounts of sulfuric acid will be.

According to the second approach, the preferred procedure is to carry out a separation by electrodialysis directly on the fermentation medium containing the lactates.

Thus patent EP 393,818 describes a process wherein the fermentation medium, from which the microorganisms have been removed, is subjected to a first, conventional electrodialysis in order to recover and concentrate the lactic acid salts in aqueous solution with the nitrogenous impurities removed, and said aqueous solution is then subjected to a second electrodialysis, this time for fractionation, in order to recover the free lactic acid and the corresponding base. The solution containing the free lactic acid then has to be treated on a strong ion exchanger in the acid form to remove the sodium ions or other cations, and the resulting solution then has to be treated on a weakly basic ion exchanger to remove all traces of sulfuric acid, sulfates or other impurities to give a purified lactic acid.

The prime disadvantages of this process are the energy cost of this system, which involves two electrodialyses in series, and the size of the volumes handled. For example, the energy cost is directly linked to the need to concentrate the solutions containing the lactic acid salts in order to perform the fractionating electrodialysis, these costs increasing proportionately to the amounts of high-purity lactic acid which it is desired to recover.

The second disadvantage relates to the phenomenon of fouling of the electrodialysis membranes.

Thus patent U.S. Pat. No. 5,681,728 insists on the need to carry out a nanofiltration step and/or to use a chelating resin as an obligatory first step in order for the concentrating or fractionating electrodialyzers to function correctly; otherwise the cost of purifying the lactic acid increases proportionately to the need to clean or replace the electrodialysis membranes.

Patent U.S. Pat. No. 5,814,498 also describes the implementation of a nanofiltration step on the clarified fermentation medium (i.e. the fermentation medium from which the lactic acid-producing microorganisms have been removed), prior to the use of bipolar fractionating electrodialysis, in order to remove the divalent cations from said fermentation medium, said cations reducing the efficiency of the electrodialysis.

Likewise, patent CA 2,227,398 describes the implementation of a nanofiltration step or a basic loop, consisting of a column of cationic resin, in order to remove the polyvalent ions before carrying out the actual electrodialysis with anionic or cationic membranes.

However, the processes improved in this way still all suffer in practice from the succession of numerous cumbersome steps which make the purification of the lactic acid from the fermentation medium particularly long and tiresome.

OBJECTS OF THE INVENTION

It is apparent from all the above that there is an unsatisfied need for a less expensive process for the separation, concentration and purification of a high-purity lactic acid, with an excellent yield, from a fermentation medium.

SUMMARY OF THE INVENTION

Anxious to develop a process which would satisfy the practical constraints better than the processes already in existence, the Applicant found that this objective could be achieved by means of a process which combined a chromatography step on a cationic exchange resin with a fractionating electrodialysis step carried out in immediate succession on the fermentation medium from which the microorganisms had been removed and which had been acidified under specific conditions.

The Applicant has thus overcome the technical prejudice whereby chromatographic separation and electrodialysis cannot be combined efficiently and directly in order to prepare a high-purity lactic acid, since it is acknowledged that each of these purification methods has to be considered independently of the other.

Thus, in patent U.S. Pat. No. 5,641,406, the additional fractionating electrodialysis step which is envisaged in the chromatographic process for the purification of lactic acid from its fermentation medium is only carried out on the dilute saline solutions in order to regenerate the base from said chromatographed saline solution and recycle it into the fermentation medium in order to regulate the pH. There is nothing here to either indicate or suggest carrying out this electrodialysis on the free lactic acid in equilibrium with its salts, contained in the chromatography fraction.

DETAILED DESCRIPTION

The process according to the invention for the separation and purification of lactic acid from a fermentation medium is characterized in that:

a) the lactic acid-producing microorganisms are separated from the other components of the fermentation medium, b) the resulting clarified aqueous solution containing the lactic acid salt(s) is concentrated, c) said concentrated aqueous solution is acidified, preferably with strong mineral acid, to a pH below or equal to 3, d) the resulting acidified aqueous solution is passed over a cation exchange resin to give a fraction consisting essentially of lactic acid in the free form and at most 25% by weight of lactic acid salt(s), expressed by dry weight relative to the dry weight of said solution, e) said fraction is optionally concentrated and then subjected to bipolar fractionating electrodialysis to give an aqueous solution enriched in lactic acid, and f) the lactic acid is purified, concentrated and recovered from said enriched aqueous solution.

The lactic acid-producing microorganisms are selected arbitrarily, especially from the group comprising Lactobacillus, Bacillus, Rhizopus and Streptococcus. The composition of their fermentation medium is widely described in the state of the art.

The pH of the fermentation medium is adjusted to a value of between 5.5 and 6.5, for example, by continuously feeding the fermentation medium with a base preferably selected from the group comprising NaOH, $Na_2CO_3$, $NaHCO_3$, $Ca(OH)_2$, $CaCO_3$, KOH and $NH_4OH$.

This results in the formation of potassium lactate, sodium lactate, calcium lactate and ammonium lactate—individually or in a mixture, depending on the chosen base(s)—in the fermentation medium. It is thus possible to regulate the pH with a mixture of potassium hydroxide and ammonia or a mixture of magnesium carbonate and calcium carbonate.

In the process according to the invention, it is advantageously preferred to regulate the pH of the fermentation medium with NaOH or $NH_4OH$, leading to the formation of sodium lactate or ammonium lactate respectively. According to the invention, all or part, preferably all, of the lactic acid contained in the fermentation medium is in the form of a salt or salts.

The first step of the process according to the invention consists in separating the lactic acid-producing microorganisms from the other components of the fermentation medium.

This separation is effected by any technique otherwise known to those skilled in the art and can consist of microfiltration, centrifugation or precipitation of said microorganisms with flocculants. These techniques can also be combined.

In the process according to the invention, the preferred technique is that of microfiltration using a microfiltration membrane whose porosity is adapted to the size of the microorganisms in question, for example TECHSEP membranes of porosity 0.1 $\mu$m for lactic acid-producing microorganisms of the genus Lactobacillus.

The second step of the process according to the invention consists in concentrating the resulting clarified aqueous solution.

The lactic acid titres of the fermentation media are conventionally rather low, i.e. between 5 and 15% by weight, so it is advisable to concentrate the lactic acid salt(s) in said clarified fermentation media before carrying out the separation steps.

This concentration step can be effected by any technique known per se to those skilled in the art, for example in a continuous evaporator at a temperature of between 50 and 65° C., preferably at a temperature of the order of 50° C.

In the process according to the invention, the lactic acid salt(s) clarified fermentation medium is concentrated to a value of between 30 and 60% by weight, preferably of between 35 and 50% and for example of the order of 40% by weight.

The third step of the process according to the invention consists in acidifying said concentrated aqueous solution, preferably with strong mineral acid, to a pH below or equal to 3.

The acidification is carried out so as to cause any lactic acid salt to dissociate into free lactic acid and its corresponding base.

In the case where the pH of the fermentation medium is regulated with ammonia, this acidification step, carried out e.g. with sulfuric acid, will dissociate the ammonium lactate into lactic acid and ammonium sulfate.

In addition, in the process according to the invention, it is chosen to acidify the concentrated clarified fermentation medium to a pH such that the resulting aqueous solution still contains at most 25% of lactic acid salt(s) in equilibrium with the free lactic acid which is thereby formed, as well as the sulfates released.

The concentrated clarified fermentation medium is therefore acidified to a pH below or equal to 3, preferably to a pH of between 1.5 and 3.

The fourth step of the process according to the invention then consists in passing the resulting acidified aqueous solution over a cation exchange resin to give a fraction consisting essentially of lactic acid in the free form and at most 25% by dry weight of lactic acid salt(s), expressed relative to the dry weight of said solution.

Passage over a strong cation exchange resin in a chromatographic separating column makes it possible preferentially to retain the lactic acid and the lactic acid salt(s) contained in said acidified solution.

This step can advantageously be performed on a strongly acidic cation exchange resin of the polystyrenesulfonic acid type crosslinked with at least 4%, preferably at least 7%, of divinylbenzene.

Virtually all the impurities in the fermentation medium can be removed in the first fractions by elution with water. Said impurities consist mainly of the unconsumed residual sugars and proteins and of the inorganic salts of the type with polyvalent ions (calcium, magnesium) and any base corresponding to any dissociated lactic acid salt. In the case where the ammonium lactate solution is treated with sulfuric acid, ammonium sulfate will be produced.

The next fractions contain lactic acid in the free form and at most 25% by dry weight of lactic acid salt(s), expressed relative to the dry weight of said solution.

The Applicant has thus observed that this ratio of free lactic acid to lactic acid salt(s), obtained through acidification of the solution to be chromatographed under the conditions of the step described above, is chosen so that the losses of free lactic acid in the first eluted fractions, i.e. with the impurities, are minimized, as will be exemplified below.

Furthermore, the consumption of sulfuric acid will be reduced because it is not necessary to acidify the clarified fermentation medium too much, and it is this which constitutes a further advantage of the process according to the invention.

After optional concentration, the fifth step of the process according to the invention consists in subjecting said fraction to bipolar fractionating electrodialysis to give an aqueous solution enriched in lactic acid.

The fraction containing the lactic acid and at most 25% of lactic acid salt(s) is therefore subjected to bipolar fractionating electrodialysis in order to dissociate any residual lactic acid salt into free lactic acid and its corresponding base.

Said fraction can be concentrated to a solids content of the order of 15 to 25% by any means known to those skilled in the art, for example by evaporation at a temperature of between 50 and 60° C.

In practice the electrodialysis is effected in a device consisting of at least two compartments and at least two bipolar membranes, it also being possible for said device to contain at least one other membrane of cationic or anionic type.

The bipolar electrodialysis device consists e.g. of seven cells, each made up of two bipolar membranes and one cationic membrane.

The operating conditions are adjusted so that less than 50 meq of cations, for example ammonium cations, remain in the electrodialyzed solution.

The last step of the process according to the invention consists in purifying, concentrating and recovering the lactic acid from said aqueous solution.

The purpose of this last step is to remove the final impurities present in the resulting electrodialyzed fraction enriched in free lactic acid, said impurities being composed mainly of the residual sugars (of the order of 0.2 to 0.3%), the ions, for example ammonium ions, which the electrodialysis could not remove completely, and the residual sulfates.

Thus it is advantageously chosen to:

a) treat said electrodialyzed aqueous solution at a temperature below 180° C., preferably of between 100 and 150° C., for 15 min to 1 h 30 min, b) pass the resulting heat-treated solution through a column of charcoal, c) demineralize the resulting solution on a strong cationic resin and then a moderately basic anionic resin, and d) concentrate the resulting purified lactic acid.

The first step serves to carbonize the residual sugars. As will be exemplified below, a possible choice is to heat at a temperature of 120° C. for 1 h.

The second step consists in decolorizing the resulting heated solution on a column of charcoal.

The third step serves to remove all the inorganic salts by passage over two resins, a strong cationic one and then a moderately basic one.

Finally, the resulting solution is concentrated in order to bring it to a solids content of at least 45% by weight, generally of between 50 and 90%.

Surprisingly and unexpectedly, analysis of the lactic acid separated and purified in this way has revealed a quality consistent with the FCC pharmaceutical standards, as will be exemplified below.

Other characteristics and advantages of the invention will become apparent from the following Examples, which are given here only by way of illustration and without implying a limitation.

EXAMPLE

A fermentation medium containing 78 g/l of ammonium lactate (expressed as lactic acid), produced by a microorganism of the genus Lactobacillus, is subjected to microfiltration on a TECHSEP membrane of porosity 0.1 μm in order to remove the cells.

The resulting clarified medium is concentrated on a vacuum evaporator at 50° C. until the ammonium lactate concentration is 40%.

The concentrated aqueous solution obtained is acidified to a pH of about 2.0 by the addition of pure sulfiric acid so that the weight ratio lactic acid/ammonium lactate is 85/15.

This acidified concentrated solution is then subjected to chromatographic separation on a strong cation exchange resin consisting of polystyrenesulfonic acid crosslinked with 7% of divinylbenzene.

It is fed in at a rate of 50 l/h.

The impurities, consisting of unconsumed proteins and sugars, ammonium sulfate and divalent cations such as $Ca^{++}$ and $Mg^{++}$, are removed in a first fraction by elution with water (280 l/h).

The second fraction, which contains lactic acid in the free form in equilibrium and is depleted in ammonium sulfate, is eluted at a rate of 130 l/h to give a concentration of 10% by weight in the final fraction.

The chromatography yield is 97%.

Said fraction, concentrated to 20% by weight, is then subjected to fractionating electrodialysis.

The electrodialyzer consists of a TOKOYAMA membranes device made up of 7 cells, marketed by EURODIA and equipped with bipolar and cationic membranes.

The configuration used combines a bipolar membrane surface area of 200 $cm^2$ with a current intensity of 100 $mA/cm^2$, i.e. 20 A overall.

3 liters of the above-mentioned fraction, concentrated to 20% and containing 600 g of lactic acid/ammonium lactate mixture and residual impurities (sugars, proteins, mineral impurities), are passed through said device for 10 minutes until the final voltage is 23 V.

After electrodialysis, the starting fraction, which contained 2 equivalents (eq) of lactic acid to 300 milliequivalents (meq) of $NH_4^+$ ions and 300 meq of $SO_4^{2-}$ ions, now contains 2 eq of lactic acid and 300 meq of $SO_4^{2-}$ ions, but only 50 meq of $NH_4^+$ ions.

The resulting electrodialyzed fraction, enriched in lactic acid, is then purified by means of a heat treatment at 120° C. for 1 h in order to remove the traces of residual proteins and sugars (0.2% by weight) which were not removed in the previous chromatographic separation step.

This carbonization leads to the formation of coloring matter, which is then removed on a column of charcoal.

Finally, a demineralization step is carried out in order to remove the $NH_4^+$, $Na^+$ and $SO_4^{2-}$ ions still present by passage over a strong cationic resin and then a moderately basic resin of the acrylic type.

The resulting solution contains 99.5% of high-purity lactic acid, expressed by dry weight. It is concentrated to a solids content of 90% by evaporation at 50° C.

The product obtained has the advantage of being perfectly consistent with the FCC standards, particularly in terms of purity and stability.

What is claimed is:

1. A process for the separation and purification of lactic acid from a fermentation medium containing said acid and lactic acid producing microorganisms, wherein said acid is totally or partially in the form of a salt or salts, wherein:

a) the lactic acid-producing microorganisms are separated from the other components of the fermentation mediums;

b) the resulting separated medium containing the lactic acid salt(s) is concentrated;

c) said concentrated separated medium is acidified to a pH below or equal to 3;

d) the resulting acidified aqueous solution is passed over a cation exchange resin to give a fraction consisting essentially of lactic acid in the free form and at most 25% by weight of lactic acid salt(s), expressed by dry weight relative to the dry weight of said solution;

e) said fraction is subjected to bipolar fractionating electrodialysis to give an aqueous solution enriched in lactic acid; and f) the lactic acid is purified, concentrated and recovered from said enriched aqueous solution.

2. A process according to claim 1, wherein said fermentation medium contains at least one lactic acid salt selected from the group comprising potassium lactate, sodium lactate, calcium lactate, and ammonium lactate.

3. A process according to claim 2 wherein the at least one lactic acid salt is ammonium lactate or sodium lactate.

4. A process according to claim 1, wherein the separation step a) is selected from the group consisting of microfiltration, centrifugation and precipitation with flocculants.

5. A process according to claim 4, wherein the separation step a) is microfiltration.

6. A process according to claim 1, wherein the concentrated separated medium obtained in step b) is acidified to a pH of between 1.5 and 3.

7. A process according to claim 1, wherein in step c), said concentrated separated medium is acidified to a pH below or equal to 3 with a strong mineral acid.

8. A process according to claim 7, wherein the strong mineral acid is sulfuric acid.

9. A process according to claim 1, wherein the cation exchange resin in step d) is a strongly acidic cation exchange resin of the polystyrenesulfonic acid type crosslinked with at least 4% of divinylbenzene.

10. A process according to claim 9, wherein the cation exchange resin in step d) is a strongly acidic cation exchange resin of the polystyrenesulfonic acid type crosslinked with at least 7%, of divinylbenzene.

11. A process according to claim 1, wherein in step e), said fraction is concentrated and then subjected to bipolar fractionating electrodialysis to give an aqueous solution enriched in lactic acid.

12. A process according to claim 1, wherein in step e), the electrodialysis is effected in a device consisting of at least two compartments and at least two bipolar membranes.

13. A process according to claim 12, wherein said device contains at least one cationic or anionic membrane.

14. A process according to claim 1, wherein, in step f), the purification and concentration of the lactic acid from the electrodialyzed aqueous solution enriched in lactic acid consists in:

a) heat treating said electrodialyzed aqueous solution at a temperature between 100 and 180° C., for 15 min to 90 min;

b) passing the resulting heat-treated solution through a column of charcoal;

c) demineralizing the resulting solution on a strong cationic resin and then a moderately basic anionic resin; and d) concentrating the resulting purified lactic acid.

15. A process according to claim 13, wherein in step a) said electrodialyzed aqueous solution is heat treated at a temperature between 100 and 150° C., for 15 min to 90 min.

* * * * *